US00PP30128P3

(12) United States Plant Patent
Brand

(10) Patent No.: US PP30,128 P3
(45) Date of Patent: Jan. 22, 2019

(54) BARBERRY PLANT NAMED 'UCONNBTB039'

(50) Latin Name: *Berberis thunbergii*
Varietal Denomination: UCONNBTB039

(71) Applicant: University of Connecticut, Farmington, CT (US)

(72) Inventor: Mark Brand, Farmington, CT (US)

(73) Assignee: University of Connecticut, Farmington, CT (US)

( * ) Notice: Subject to any disclaimer, the term of this patent is extended or adjusted under 35 U.S.C. 154(b) by 0 days.

(21) Appl. No.: 15/330,051

(22) Filed: Jul. 30, 2016

(65) Prior Publication Data

US 2018/0035589 P1 Feb. 1, 2018

(51) Int. Cl.
*A01H 5/00* (2018.01)
*A01H 5/08* (2018.01)

(52) U.S. Cl.
USPC ..... Plt./241
CPC ..... *A01H 5/08* (2013.01)

(58) Field of Classification Search
USPC ..... Plt./241
See application file for complete search history.

(56) References Cited

U.S. PATENT DOCUMENTS

PP8,215 P 4/1993 Moretti

OTHER PUBLICATIONS

Lehrer et al. (Scientia Horticulturae 119: 67-71, 2008).*
Co-pending U.S. Appl. No. 15/330,050, filed Jul. 30, 2016.
Co-pending U.S. Appl. No. 15/330,049, filed Jul. 30, 2016.
Co-pending U.S. Appl. No. 15/330,048, filed Jul. 30, 2016.

* cited by examiner

*Primary Examiner* — Keith O. Robinson
(74) *Attorney, Agent, or Firm* — Michael Best & Friedrich LLP

(57) ABSTRACT

The present invention relates to a new and distinct cultivar of Barberry plant, botanically known as *Berberis thunbergii* and hereinafter referred to by the name 'UCONNBTB039'. The unique characteristics of this new Barberry plant include no fruit, seed sterile; compact, dense, spreading habit with overarching stems reaching 70 cm tall; bright green spring foliage and dark green summer foliage; adaptable to many landscape situations; resistant to black stem rust disease; and winter cold hardy to at least −26° C.

4 Drawing Sheets

FEDERAL FUNDING

This invention was made with government support under 2015-31200-06009 awarded by the USDA. The government has certain rights in the invention.

BACKGROUND OF THE INVENTION

The present invention relates to a new and distinct cultivar of Barberry plant, botanically known as *Berberis thunbergii* and hereinafter referred to by the name 'UCONNBTB039'.

The new Barberry plant is a product of a planned breeding program conducted in Storrs, Conn. The new Barberry plant was developed by exposing pre-germinated seed to the mitotic inhibitor colchicine to create an autotetraploid plant. Specific methods used followed those published in Lehrer, J. M., M. H. Brand, J. D. Lubell, "Induction of tetraploidy in meristematically active seeds of Japanese barberry (*Berberis thunbergii* var. *atropurpurea*) through exposure to colchicine and oryzalin", *Scientia Horticulturae* 119:67-71 (2008). Briefly, seeds were cold stratified for 4-6 weeks and then pre-germinated seeds with 5-7 mm of radicle emergence were exposed to a 0.1% colchicine solution for 24 hours. The maternal parent plant that provided the seed is *Berberis thunbergii* var. *atropurpurea*. *Berberis thunbergii* var. *atropurpurea*, which is not patented, and has been used in the nursery industry since the mid-1920's. The paternal parent is unknown since the seed used was open pollinated. Treated seeds were then planted in flats and grown in a greenhouse until they were large enough for ploidy analysis by flow cytometry. Seedlings that were tetraploids were grown on for further evaluation. Tetraploidy was confirmed multiple times by flow cytometry when plants were in containers and the field.

One hundred tetraploid plants were created in early 2005 and grown in a greenhouse and coldframe for their first growing season. Tetraploid plants were grown outdoors in containers during 2006 to 2010 and were evaluated for horticultural traits and fruit and seed production. In spring 2011, tetraploid plants were planted in the field for long term evaluation. Diploid *Berberis thunbergii* var. *atropurpurea* plants were grown in the same planting as tetraploid plants to serve as control plants. During the growing seasons of 2012, 2013, and 2014, tetraploid plants established in the field were evaluated for fruit production, seed production, seed germination and seedling ploidy in comparison to diploid control plants. *Berberis thunbergii* 'UCONNBTB039' was selected from among 100 tetraploid seedlings based on lack of seed production, vigorous growth, compact habit, and spreading form.

Asexual reproduction of *Berberis thunbergii* 'UCONNBTB039' by softwood stem cuttings (since 2012) made in late June through early July in a greenhouse or container nursery environment has shown that the unique features of this new barberry plant are stable and reproduced true-to-type in successive generations of asexual reproduction.

SUMMARY OF THE INVENTION

Plants of the new Barberry have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of the new Barberry plant: dense, spreading, overarching habit growing to approximately 70 cm tall by 120 cm wide in 10 years; bright green spring foliage and with dark green summer foliage; foliage thick and slightly leathery, held on stout stems; fall foliage color is orange; a limited number of light yellow flowers, held singly, can be produced in late April-early May in Connecticut, but they are not numerous; fruits and seeds have not been observed, while the diploid maternal parent *Berberis thunbergii* var. *atropurpurea* produces many viable seeds; cold hardy in winter to at least −26° C.; tested to be resistant to black stem rust by the USDA Cereal Diseases Laboratory in St. Paul, Minn.

These characteristics in combination distinguish *Berberis thunbergii* 'UCONNBTB039' as a new and distinct Barberry plant:

1. no fruit, seed sterile;
2. compact, dense, spreading habit with overarching stems reaching 70 cm tall;
3. bright green spring foliage and dark green summer foliage;
4. adaptable to many landscape situations;
5. resistant to black stem rust disease; and
6. winter cold hardy to at least −26° C.

Plants of the new Barberry can be compared to plants of the female parent *Berberis thunbergii* var. *atropurpurea*. Plants of the new Barberry differ primarily from plants of *Berberis thunbergii* var. *atropurpurea* in that 'UCONNBTB039' is sterile, while the diploid maternal parent *Berberis thunbergii* var. *atropurpurea* produces thousands of seeds per plant per year. In addition, 'UCONNBTB039' does not grow as large as *Berberis thunbergii* var. *atropurpurea*, reaching only 70 cm tall and 120 cm wide in 10 years, while *Berberis thunbergii* var. *atropurpurea* grows to 130 cm tall and 170 cm wide in 10 years. 'UCONNBTB039' has green foliage, while *Berberis thunbergii* var. *atropurpurea* has burgundy red summer foliage. The leaves of 'UCONNBTB039' are similar in size and shape to those of *Berberis thunbergii* var. *atropurpurea*, but they are slightly thicker and more leathery.

Plants of the new Barberry can be compared to the unpatented commercial variety *Berberis* 'Emerald Carousel'. These varieties are similar in most horticultural characteristics; however 'UCONNBTB039' differs in the following:

1. Very compact plant habit, whereas this comparator is a large plant with a spreading habit.
2. Very low or no female fertility or fruit production, whereas this comparator is highly fruitful.

BRIEF DESCRIPTION OF THE PHOTOGRAPHS

The accompanying colored photographs illustrate the overall appearance of the new Barberry plant showing the colors as true as it is reasonably possible to obtain in colored reproductions of this type. Colors in the photographs may differ slightly from the color values cited in the detailed botanical description which accurately describe the colors of the new Barberry plant.

DETAILED BOTANICAL DESCRIPTION

Figure 1:
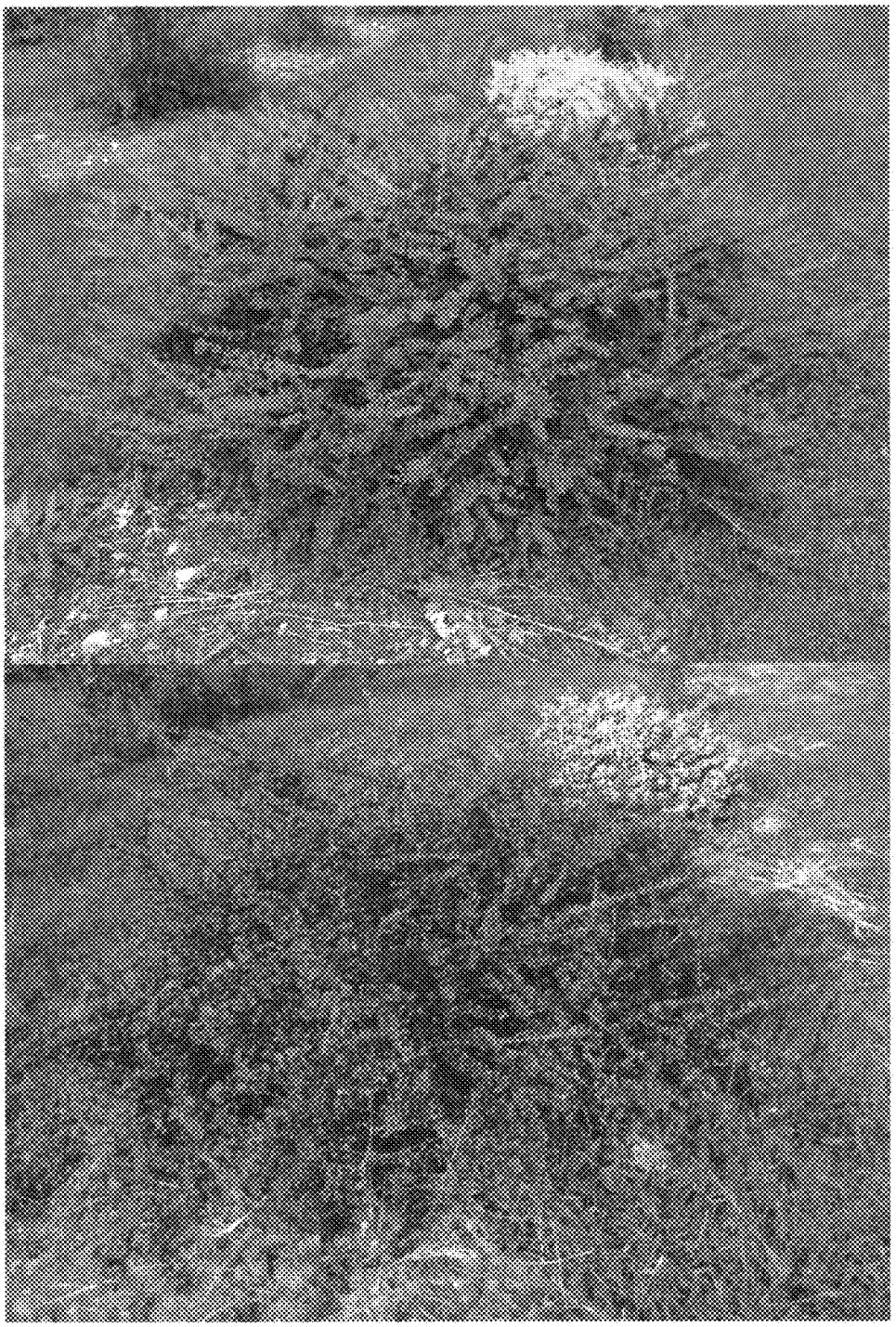
FIG. 1 shows a field grown plant of 'UCONNBTB039' as it appears in spring (top image) and then later in the summer (bottom image).
Figure 2:
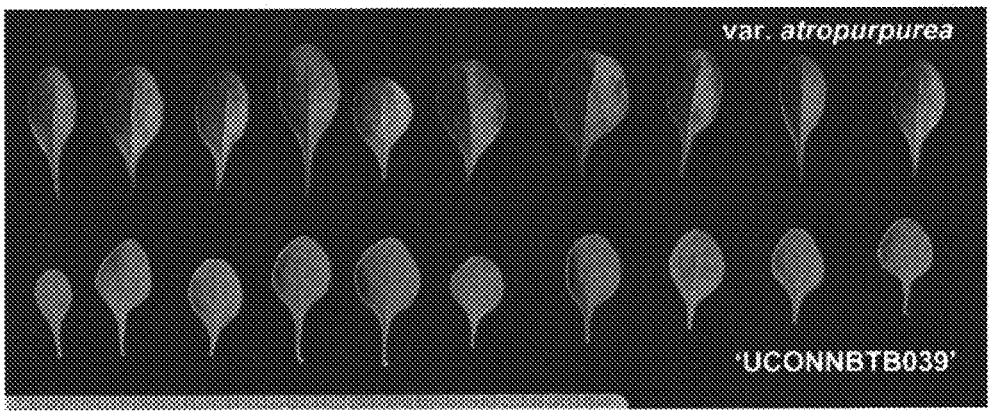
FIG. 2 shows a close up comparison of leaves from *Berberis thunbergii* var. *atropurpurea* (top row) and 'UCONNBTB039' (bottom row).
Figure 3:
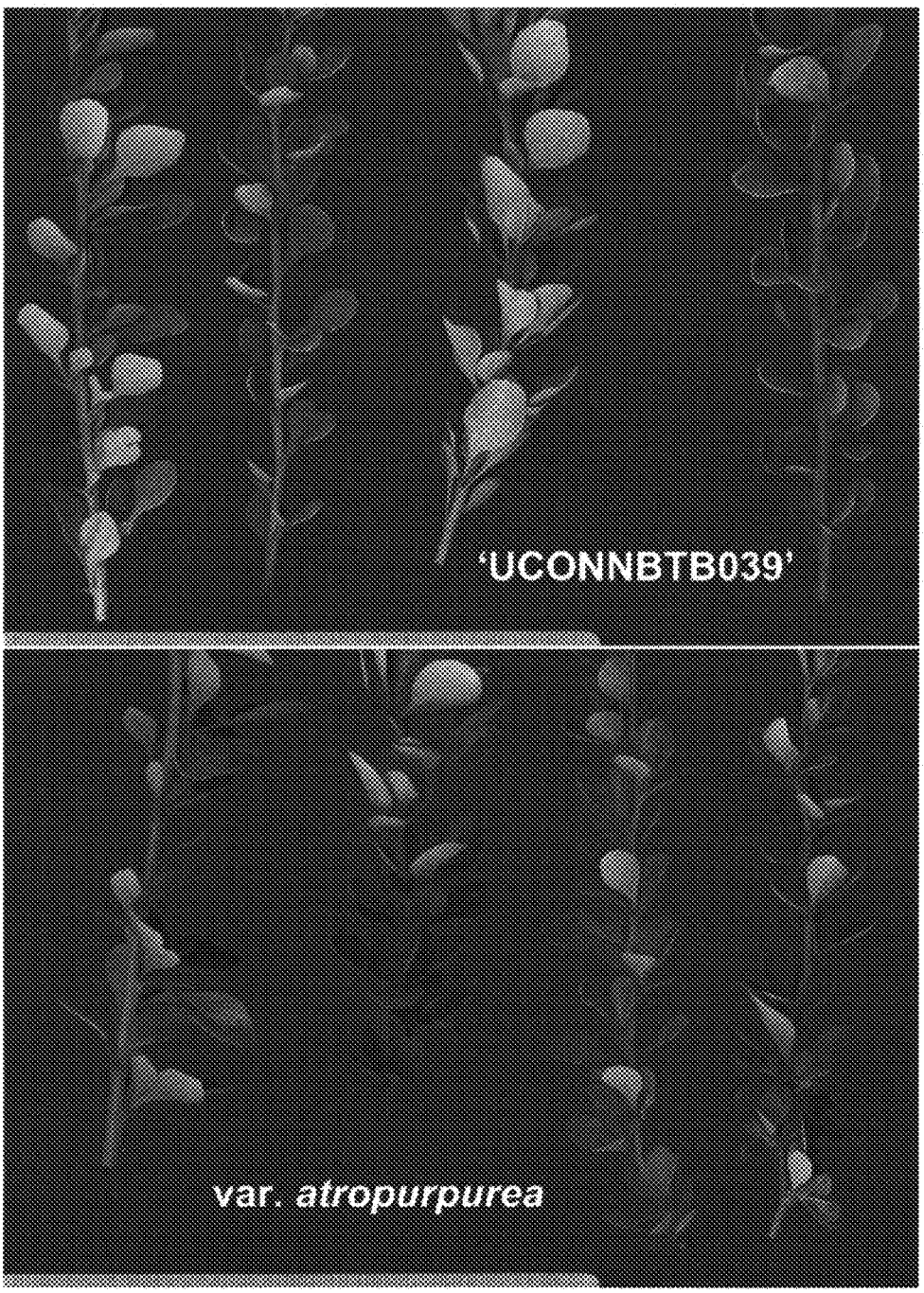
FIG. 3 shows the summer shoots of 'UCONNBTB039' in comparison to *Berberis thunbergii* var. *atropurpurea.*
Figure 4:
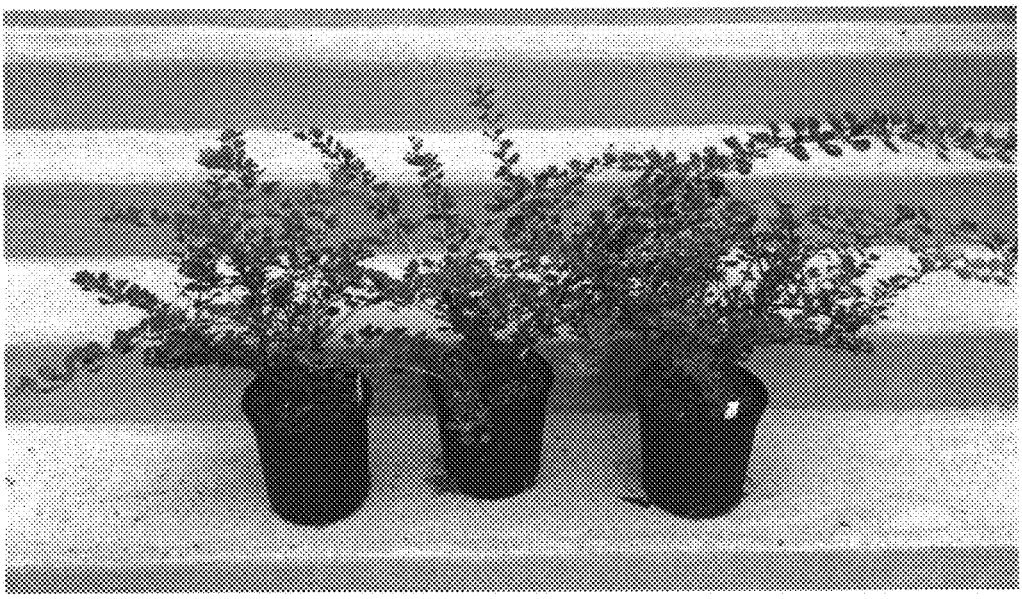
FIG. 4 shows three container grown plants of 'UCONNBTB039' at the beginning of their second summer of growth since propagation. These plants were rooted from softwood cuttings two summers prior.

The aforementioned photographs and following observations, measurements and values describe plants grown during the spring, summer, or fall in ground beds or container, in an outdoor nursery in Storrs, Conn. and under cultural practices which closely approximate commercial Barberry production. Plants used for most photographs and description were 10 years old. In the following detailed description, color references are made to The Royal Horticultural Society Colour Chart, 1995 Edition, except where general terms of ordinary dictionary significance are used.

Botanical classification: *Berberis thunbergii* 'UCONNBTB039'.

Parentage:

*Female, or seed, parent.*—*Berberis thunbergii* var. *atropurpurea.*

*Male, or pollen, parent.*—Unknown. Open pollinated seed was used to create the new barberry.

Propagation:

*Type.*—Softwood stem cutting.

*Time to initiate roots, summer.*—About 6 weeks at daytime temperatures between 75-90° F.

*Time to produce a rooted young plant, summer.*—About 8-12 weeks at temperatures between 75-90° F.

*Root description.*—2-6 roots per cutting, yellow to brown in color and not effectively measured with a color chart.

*Rooting habit.*—Fibrous root system develops from the initial adventitious roots.

Plant description:

*Plant form and growth habit.*—Low, dense, mounded, compact plant, typically wider than tall.

*Plant height.*—About 70 cm tall in 10 years.

*Plant diameter* (*area of spread*).—About 120 cm wide in 10 years.

*Plant vigor.*—Strong.

Lateral branch description:

*Length.*—Typically between 20 to 30 cm, but some shoots can exceed 50 cm.

*Diameter.*—About 1 mm to 4 mm, typically 3 mm.

*Internode length.*—Between 10 to 15 mm, mostly 11 to 12 mm.

*Aspect.*—Upright and spreading from the plant center; overarching.

*Strength.*—Firm and stiff.

*Texture.*—Fine.

*Color*.—Close to 146C yellow-green on new, current season shoots; changing to close to 200B brown group as the stems mature. Stems older than 1-2 seasons have a color closer to 202D black group mixed with 200B brown group.

*Thorns*.—Quantity: single at most nodes. Length: 10-12 mm. Width at the base: 1 mm. Color: 146D at base, changing to 183 B at tip.

Leaf description:

*Arrangement*.—Whorled in rosette on spur shoots; alternate down long shoots, but typically 2-4 leaves at each node.

*Length*.—About 25-30 mm, typically ranging from 20-35 mm.

*Width*.—About 14-16 mm, typically ranging from 10-18 mm.

*Shape*.—Obovate to spatulate-oblong.

*Apex*.—Typically obtuse, sometimes with small spine at tip.

*Base*.—Narrowing to only petiole; very acute.

*Margin*.—Entire.

*Texture, upper and lower surfaces*.—Glabrous.

*Venation pattern*.—Pinnate.

*Color*.—Developing leaves, upper surface: Close to yellow-green group 144A and green group 143A.

*Developing leaves, lower surface*.—Close to green group 138B and yellow-green group 146B.

*Fully expanded leaves, upper surface*.—Close to 139A and 136A green group.

*Fully expanded leaves, lower surface*.—Close to 138A and 137C green group.

*Petiole*.—Length: About 1-14 mm. Diameter: About 1 mm. Texture, upper and lower surfaces: glabrous. Color, upper and lower surfaces: RHS 139A and 136A green.

*Persistence of foliage*.—Deciduous.

*Glossiness of the leaf*.—Medium.

Flower description:

*Flower arrangement and habit*.—Typically solitary, but produced infrequently.

*Fragrance*.—None noted.

*Natural flowering season*.—April in Storrs, Conn.

*Flower longevity*.—7 to 14 days depending on weather conditions.

*Inflorescence length*.—About 15 mm; ranging from about 10-20 mm.

*Inflorescence diameter*.—About 12 mm.

*Inflorescence type*.—Typically solitary. Axial occurring along underside of branches.

*Number of flowers per inflorescence*.—1.

*Flower diameter*.—About 12 mm; ranging from 10-15 mm.

*Flower length (height)*.—About 5.75 mm; ranging from 5-7 mm.

*Flower buds*.—Length: About 4 mm. Diameter: About 6 mm. Shape: Rounded. Color: Close to 11A to 11B, yellow group.

*Petals*.—Arrangement: 6 petals in a single whorl.

*Length*.—About 4-5 mm.

*Width*.—About 3-4 mm.

*Shape*.—Cupped.

*Apex*.—Rounded to acute.

*Margin*.—Smooth.

*Texture, upper and lower surfaces*.—Both glabrous.

*Color*.—When opening and fully open, adaxial and abaxial surfaces: 12C yellow group.

*Sepals*.—Arrangement: 6 to 8 sepals in a single whorl. Length: About 7 mm. Width: About 4 mm. Shape: cupped. Apex: rounded to acute. Base: straight-sided, tapering. Margin: smooth. Texture, upper and lower surfaces: glabrous. Color: Fully developed, adaxial surface: Close to 11C, yellow group. Fully developed, abaxial surface: Close to 11B yellow group.

*Pedicels*.—Length: About 4-6 mm. Diameter: About 1 mm. Aspect: About 45-60 degree from peduncle axis. Color: Close to 154A, yellow-green group.

*Reproductive organs*.—Stamens: Quantity: 6. Anther shape: flat to cupped, narrow. Anther length: About 4 mm. Anther color: Close to 12C. Pollen amount: Scarce and sticky. Pollen color: Near RHS yellow 12A. Pistils: Quantity: 1 per flower. Pistil length: About 3 mm. Style length: About 1-2 mm. Style color: Close to 154B. Stigma color: Close to 154B. Ovary color: Close to 154B. Seeds and fruits: Fruit development has been observed on plants of the new Barberry, but only a very small number of fruits have been observed. To date, fruits have been devoid of seeds. Fruit shape: Elliptical, 7-10 mm long and 4-5 mm in diameter. Fruit color: RHS color near red 53B. Fruit waxiness: Glossy.

Garden performance: Plants of the new Barberry have been observed to have excellent garden performance and tolerate a wide range of environmental conditions and temperatures ranging from about −26° C. to about 40° C.

Pathogen & pest resistance: Plants of the new Barberry have been observed to be resistant to black stem rust (*Puccinia graminis* f. sp. *tritici*). Plants of the new Barberry have not been shown to be resistant to pests and other pathogens common to Barberry plants.

It is claimed:

1. A new and distinct Barberry plant named 'UCONNBTB039' as illustrated and described.

* * * * *